US012105771B2

United States Patent
Heo et al.

(10) Patent No.: US 12,105,771 B2
(45) Date of Patent: Oct. 1, 2024

(54) APPARATUS AND METHOD FOR GENERATING TRAINING DATA

(71) Applicant: AJOU UNIVERSITY INDUSTRY-ACADEMIC COOPERATION FOUNDATION, Suwon-si (KR)

(72) Inventors: Jae Sung Heo, Seoul (KR); Chul Ho Kim, Seoul (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 374 days.

(21) Appl. No.: 17/455,513

(22) Filed: Nov. 18, 2021

(65) Prior Publication Data

US 2022/0156515 A1 May 19, 2022

(30) Foreign Application Priority Data

Nov. 19, 2020 (KR) .................. 10-2020-0155256

(51) Int. Cl.
*G06F 18/214* (2023.01)
*G06N 20/00* (2019.01)
(Continued)

(52) U.S. Cl.
CPC .......... *G06F 18/214* (2023.01); *G06N 20/00* (2019.01); *G06T 7/0012* (2013.01); *G16H 30/20* (2018.01);
(Continued)

(58) Field of Classification Search
None
See application file for complete search history.

(56) References Cited

U.S. PATENT DOCUMENTS

2020/0160981 A1* 5/2020 Masubuchi .............. G06N 3/08

FOREIGN PATENT DOCUMENTS

KR        10-1352999 B1     2/2014
KR    10-2014-0107737 A    9/2014
(Continued)

OTHER PUBLICATIONS

Korean Office Action dated May 29, 2022 in App. No. 10-2020-0155256.

*Primary Examiner* — Leon Flores
(74) *Attorney, Agent, or Firm* — Sughrue Mion, PLLC

(57) ABSTRACT

Disclosed are an apparatus and method for generating training data. An apparatus for generating training data according to an embodiment includes a reading result acquirer that acquires one or more oral endoscopic images and clinical information related to each of the one or more oral endoscopic images, provides the one or more oral endoscopic images and the clinical information to a user terminal of each of a plurality of preset medical staffs, and receives a reading result for each of the one or more oral endoscopic images from the user terminal of each of the plurality of medical staffs, and a labeling unit that selects one or more labeling target images from among the one or more oral endoscopic images based on the reading result received from the user terminal of each of the plurality of medical staffs and determines one or more labels for each of the one or more labeling target images based on the reading result.

6 Claims, 7 Drawing Sheets

(51) Int. Cl.
*G06T 7/00* (2017.01)
*G16H 30/20* (2018.01)

(52) U.S. Cl.
CPC ............... *G06T 2207/10068* (2013.01); *G06T 2207/30036* (2013.01); *G06T 2207/30096* (2013.01); *G06V 2201/03* (2022.01)

(56) References Cited

FOREIGN PATENT DOCUMENTS

KR 10-2018-0040287 A 4/2018
KR 10-2151943 B1 9/2020

* cited by examiner

APPARATUS AND METHOD FOR GENERATING TRAINING DATA

CROSS-REFERENCE TO RELATED APPLICATION

This application claims the benefit under 35 USC § 119(a) of Korean Patent Application No. 10-2020-0155256, filed on Nov. 19, 2020, in the Korean Intellectual Property Office, the entire disclosure of which is incorporated herein by reference for all purposes.

BACKGROUND

1. Field

The disclosed embodiments relate to a technique for generating training data.

2. Description of Related Art

According to statistics on a cause of death, diseases with the highest mortality rate is known to be cancer. Among the diseases, oral cancer does not correspond to a common cancer disease. However, oral cancer has a relatively high rate of misdiagnosis compared to its low incidence. That is, oral cancer can be viewed as one of the diseases with a high possibility of reading errors during medical treatment. In addition, as the detection time of oral cancer is delayed, a survival rate of oral cancer is rapidly reduced compared to other diseases. Accordingly, oral cancer requires a core treatment that can suspect oral cancer during endoscopic examination by primary medical treatment. Therefore, it is important for oral cancer to be accurately diagnosed through an initial medical testing by closely analyzing the characteristics of anatomical tissue through an oral endoscopy image.

However, endoscopic imaging is a simple and effective method for diagnosing oral diseases, including oral cancer, but the number of specialists who can accurately read an endoscopic image is insufficient, and the number of experienced doctors is relatively limited due to the fact that oral cancer does not occur more frequently than patients who complain of benign oral mucosal disease. In addition, although some of expression patterns of oral cancer are accompanied by thickening of epithelial cells, there is a problem in that it is difficult to differentiate from stomatitis when expressed as a mucosal ulcer.

Therefore, in order to develop a more precise oral endoscopic image reading method, a method of designing an algorithm through machine learning can be prepared as a solution, but such a solution requires that a machine learning model be trained based on reliable training data.

SUMMARY

The disclosed embodiments are intended to provide an apparatus and method for generating training data.

According an aspect of the disclosure, there is provided a method for generating training data according to an embodiment includes acquiring one or more oral endoscopic images and clinical information related to each of the one or more oral endoscopic images, providing the one or more oral endoscopic images and the clinical information to a user terminal of each of a plurality of preset medical staffs, receiving a reading result for each of the one or more oral endoscopic images from the user terminal of each of the plurality of medical staffs, selecting one or more labeling target images from among the one or more oral endoscopic images based on the reading result received from the user terminal of each of the plurality of medical staffs, and determining one or more labels for each of the one or more labeling target images based on the reading result.

In the acquiring, a malignant, an oral endoscopy image corresponding to malignant, benign, or normal may be acquired based on clinical findings of a specialist on the one or more oral endoscopic images included in the clinical information.

In the selecting, an oral endoscopy image, for which more than half of lesion classification results judged by each of a plurality of medical staffs are the same, among the one or more oral endoscopy images may be selected as the labeling target image, based on the reading result.

The reading result may include at least one of a classification result, a position, and a boundary of a lesion included in each of the one or more oral endoscopic images.

In the determining, a classification result for which more than half of the classification results of the lesions judged by each of the plurality of medical staffs match may be determined as a label.

In the determining, an average position of positions of the lesions judged by each of the plurality of medical staffs may be determined as a label.

In the determining, an average boundary of boundaries of the lesions judged by each of the plurality of medical staffs may be determined as a label.

According another aspect of the disclosure, there is provided an apparatus for generating training data includes a reading result acquirer that acquires one or more oral endoscopic images and clinical information related to each of the one or more oral endoscopic images, provides the one or more oral endoscopic images and the clinical information to a user terminal of each of a plurality of preset medical staffs, and receives a reading result for each of the one or more oral endoscopic images from the user terminal of each of the plurality of medical staffs and a labeling unit that selects one or more labeling target images from among the one or more oral endoscopic images based on the reading result received from the user terminal of each of the plurality of medical staffs and determines one or more labels for each of the one or more labeling target images based on the reading result.

The reading result acquirer may acquire, an oral endoscopy image corresponding to malignant, benign, or normal based on clinical findings of a specialist on the one or more oral endoscopic images included in the clinical information.

The labeling unit may select an oral endoscopy image, for which more than half of lesion classification results judged by each of a plurality of medical staffs are the same, among the one or more oral endoscopy images as the labeling target image, based on the reading result.

The reading result may include at least one of a classification result, a position, and a boundary of a lesion included in each of the one or more oral endoscopic images.

The labeling unit may determine a classification result for which more than half of the classification results of the lesions judged by each of the plurality of medical staffs match as a label.

The labeling unit may determine an average position of positions of the lesions judged by each of the plurality of medical staffs as a label.

The labeling unit may determine an average boundary of boundaries of the lesions judged by each of the plurality of medical staffs as a label.

According to the disclosed embodiments, training data can be generated based on the reading results obtained by diagnosing oral endoscopy images by a plurality of medical staffs having specialized knowledge on oral cancer, thereby capable of generating reliable training data.

DETAILED DESCRIPTION

Hereinafter, a specific embodiment will be described with reference to the drawings. The following detailed description is provided to aid in a comprehensive understanding of the methods, apparatus and/or systems described herein. However, this is illustrative only, and the present disclosure is not limited thereto.

In describing the embodiments, when it is determined that a detailed description of related known technologies related to the present disclosure may unnecessarily obscure the subject matter of the disclosed embodiments, a detailed description thereof will be omitted. In addition, terms to be described later are terms defined in consideration of functions in the present disclosure, which may vary according to the intention or custom of users or operators. Therefore, the definition should be made based on the contents throughout this specification. The terms used in the detailed description are only for describing embodiments, and should not be limiting. Unless explicitly used otherwise, expressions in the singular form include the meaning of the plural form. In this description, expressions such as "comprising" or "including" are intended to refer to certain features, numbers, steps, actions, elements, some or combination thereof, and it is not to be construed to exclude the presence or possibility of one or more other features, numbers, steps, actions, elements, parts or combinations thereof, other than those described.

Figure 1:
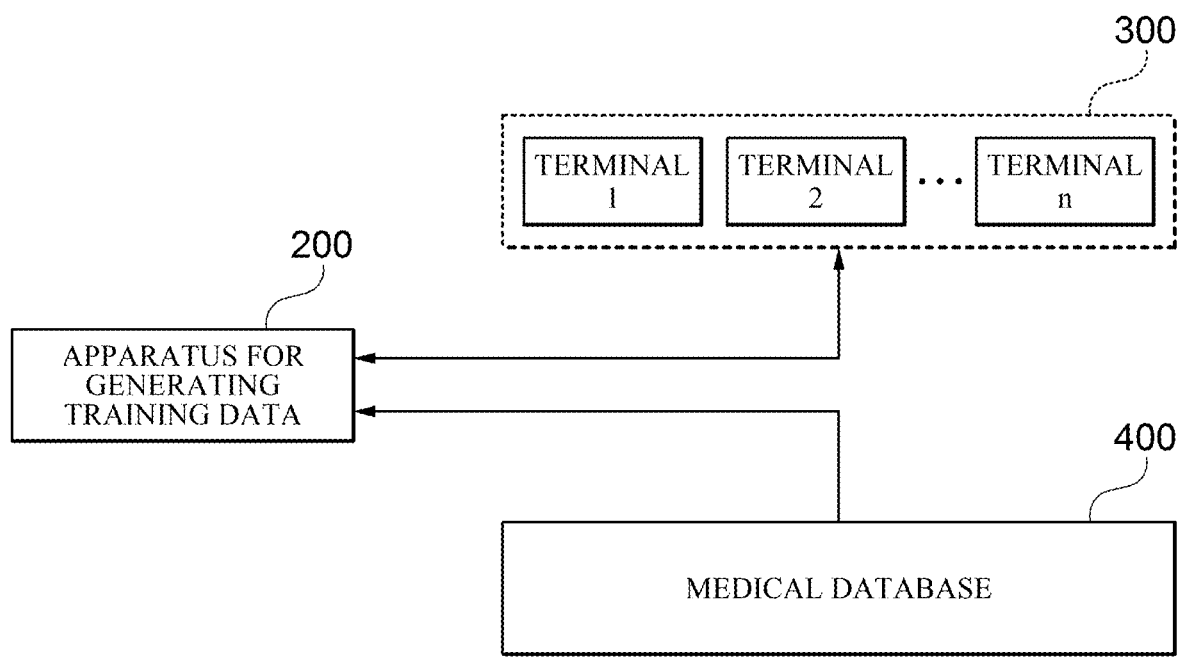
FIG. 1 is a block diagram for describing a system for generating training data according to an embodiment.

FIG. 1 is a block diagram for describing a system 100 for generating training data according to an embodiment.

Referring to FIG. 1, the system 100 for generating training data includes an apparatus 200 for generating training data, a plurality of user terminals 300, and a medical database 400.

The apparatus 200 for generating training data acquires one or more oral endoscopic images and clinical information corresponding to the oral endoscopic images from the medical database 400, and then provides the acquired oral endoscopic images and clinical information to each of the plurality of user terminals 300 used by different medical staffs. Thereafter, the apparatus 200 for generating training data determines a label for at least one of one or more oral endoscopy images based on a reading result of each medical staff for the oral endoscopy images provided to the user terminal 300 of each medical staff.

The plurality of user terminals 300 are user terminals that are respectively used by the plurality of medical staffs. In this case, the plurality of medical staffs may be head and neck specialist surgeons.

Each user terminal 300 can receive the oral endoscope image and clinical information on the oral endoscopy image from the apparatus 200 for generating training data and display the oral endoscope image and clinical information on a display screen, and receive a reading result for the oral endoscope image displayed on the display screen as an input from the medical staff. In addition, each user terminal 300 provides the input reading result to the apparatus 200 for generating training data.

In addition, although the plurality of user terminals 300 are illustrated as including terminals 1 to n in FIG. 1, according to an embodiment, the plurality of user terminals 300 may include two or more user terminals.

Meanwhile, the plurality of user terminals 300 may be, for example, devices such as a tablet PC, a laptop PC, and a smart phone, but are not necessarily limited to a specific type of device. In addition to the examples described above, the plurality of user terminals 300 may be various types of devices capable of communicating with the apparatus 200 for generating training data through a wired or wireless network.

The medical database 400 is, for example, a database that stores an oral endoscopy image and clinical information (pathology report) photographed for the diagnosis of oral cancer. For example, the medical database 400 may be any one of an electronic medical record (EMR) system and a picture archiving and communication system (PACS) operated by each hospital.

Figure 2:
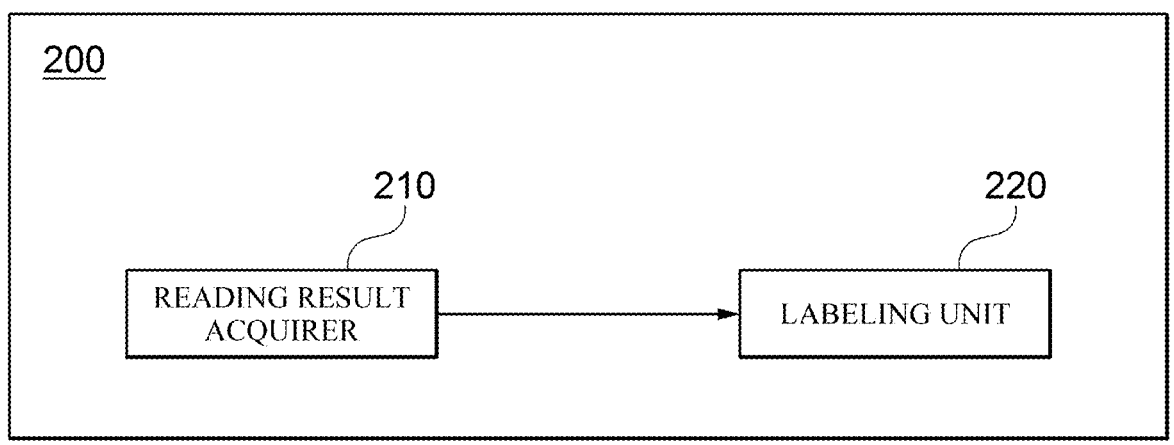
FIG. 2 is a block diagram illustrating a configuration of an apparatus for generating training data according to an embodiment.

FIG. 2 is a block diagram illustrating a configuration of the apparatus 200 for generating training data according to an embodiment.

Referring to FIG. 2, the apparatus 200 for generating training data according to an embodiment includes a reading result acquirer 210 and a labeling unit 220.

According to one embodiment, the reading result acquirer 210 and the labeling unit 220 may be implemented using one or more physically separated devices, or implemented by one or more processors or a combination of one or more processors and software, and may not be clearly distinguished in a specific operation unlike the illustrated example.

The reading result acquirer 210 acquires one or more oral endoscopic images and clinical information related to each of the one or more oral endoscopic images and provides the acquired one or more oral endoscopic images and clinical information to a user terminal of each of a plurality of preset medical staffs. In addition, the reading result acquirer 210 receives the reading result for each of the one or more oral endoscope images from the user terminal of each of the plurality of medical staffs.

According to an embodiment, the oral endoscopic image acquired by the reading result acquirer 210 is an image stored in the medical database 400 such as EMR or PACS, and can be an image photographed with an endoscope for diagnosing oral cancer.

According to an embodiment, the reading result acquirer 210 can acquire an oral endoscopic image corresponding to malignant, benign, or normal based on clinical findings of the medical staff on one or more oral endoscopic images included in the clinical information. For example, the reading result acquirer 210 may aim to acquire a total of 10,000 or more oral endoscopic images.

Specifically, the reading result acquirer 210 can acquire 3,000 or more oral endoscopic images selected as malignant based on the clinical findings of the specialist. In this case, the oral endoscopic image selected as malignant may be, for example, an oral endoscopic image in which a malignant lesion is confirmed (oral endoscopy image of a patient who was suspected of malignancy according to the clinical findings of a head and neck specialist surgeon and was subjected to follow-up biopsy) or an oral endoscopic image of a patient determined to be oral cancer in a follow-up biopsy (oral endoscopy image of a patient diagnosed with oral cancer based on a pathology document).

In addition, the reading result acquirer 210 can acquire 3,000 or more oral endoscopic images selected as benign based on the clinical findings of the specialist. In this case, the oral endoscopic image selected as normal may be, for example, an oral endoscopic image in which a benign lesion is confirmed (oral endoscopy image of a patient confirmed to be the benign lesion based on the clinical findings of a head and neck specialist surgeon) or an oral endoscopic image of a patient diagnosed with a pathologically benign oral disease when surgery or biopsy was performed.

In addition, the reading result acquirer 210 can acquire 4000 or more oral endoscopic images selected as normal based on the clinical findings of the specialist. In this case, the oral endoscopic image selected as normal may be, for example, an oral endoscopic image of a patient confirmed to be normal based on the clinical findings of the head and neck specialist surgeon.

According to one embodiment, the reading result acquirer 210 can provide clinical information together to the plurality of user terminals 300 related to the oral endoscopic image in order to help a correct diagnosis for the oral endoscopic image provided to the plurality of user terminals 300.

In this case, clinical information includes basic information including an age, gender, and race information of a patient, disease-related past history information, patient personal habit information converted to flag form rather than history format, and pathology findings of the patient and a diagnosis name. Specifically, clinical information may further include demographic information (e.g., age, gender, race at the point in time when oral endoscopy image was captured), the date and time oral endoscopy image was captured, the shape of the oral endoscopy image, device information (e.g., model name, manufacturer name) of the oral endoscopy image, a biopsy and pathology report of malignant of oral endoscopy image, the date and time of the biopsy, etc.

Meanwhile, according to an embodiment, the reading result received from each user terminals 300 may include at least one of a classification result, position, and boundary of a lesion included in the oral endoscopic image provided to each user terminals 300. The type of oral lesion that can be classified by user terminals 300 is not particularly limited, and various oral lesions that may occur in the oral cavity may be provided to user terminals 300. An example of a readable oral lesion can be referred to the following paper. However, it should be noted that the examples described in the paper do not limit the scope of the invention described in the present specification.

"Gonsalves, Wanda C., Angela C. Chi, and Brad W. Neville.
"Common oral lesions: Part II. Masses and neoplasia."
American family physician 75.4 (2007): 509-512"

Specifically, the classification result of the lesion may include a judgment result of whether or not the oral endoscopic image provided from the plurality of user terminals 300 is malignant, benign, or normal.

In addition, the boundary of the lesion may be a closed curve displayed in the provided oral endoscopic image by each of a plurality of medical staffs to specify the position of the lesion.

In addition, the position of the lesion may be a central position of an area surrounded by a closed curve calculated by displaying the displayed closed curve on a coordinate plane.

The labeling unit 220 selects one or more labeling target images from among one or more oral endoscopic images based on the reading result received from the user terminal of each of the plurality of medical staffs. In addition, the labeling unit 220 determines one or more labels for is each of the one or more labeling target images based on the received reading result.

According to an embodiment, the labeling unit 220 can select, as the labeling target image, an oral endoscopy image, for which more than half of the lesion classification results judged by each of the plurality of medical staffs are the same, among one or more oral endoscopy images.

When the reading results of a plurality of specialists on the oral endoscopy image do not match by more than half, the reading results for the oral endoscopy image have low reliability, and thus it is inappropriate to select the oral endoscopy image as the labeling target image. Therefore, only an oral endoscopic image having reliability greater than or equal to a fixed standard can be selected as the labeling target image.

According to an embodiment, the labeling unit 220 can determine the classification result, for which more than half of the classification results of lesions judged by each of the plurality of medical staffs match as a label.

In addition, according to an embodiment, the labeling unit 220 can determine an average position of positions of the lesion judged by each of the plurality of medical staffs as the label.

In addition, according to an embodiment, the labeling unit 220 may determine an average boundary of boundaries of the lesion judged by each of the plurality of medical staffs as the label.

Meanwhile, since the reading result acquirer 210 receives the reading results diagnosed by the plurality of medical staffs, not all items included in each reading result may match. Accordingly, the labeling unit 220, in order to determine the label for the oral endoscopic image based on the reading results received from the plurality of user terminals 300, can determine the classification result of the lesion which matches more than half among the classification results of the lesion, as a classification result for the corresponding oral endoscopy image.

For example, in order for the classification result of the lesion to be labeled as a normal class, each of the reading results diagnosed by the plurality of medical staffs may be, for example, normal, normal, and benign. That is, the normal class can be determined as a label for the corresponding oral endoscopic image only when all of the lesion classification results according to the reading result match the normal class, or the lesion classification result that matches more than half among the lesion classification results corresponds to the normal class.

However, since the boundary of the lesion is marked according to subjectivity of each medical staff, a possibility that portions marked by the plurality of medical staffs as the boundaries of the lesion are exactly the same may be low. That is, the labeling unit 220 can determine an average value of the lesion boundaries marked by each of the plurality of medical staffs as the label for the corresponding oral endoscopy image in order to determine the label for the oral endoscopic image based on the lesion boundary marked by each of the plurality of medical staffs, The position of the lesion can be specified from the boundary of the lesion. That is, the labeling unit 220 can similarly determine the average value of the center positions of the areas surrounded by the closed curves displayed by each of the plurality of medical staffs as the label of the corresponding oral endoscopic image.

Figure 3:
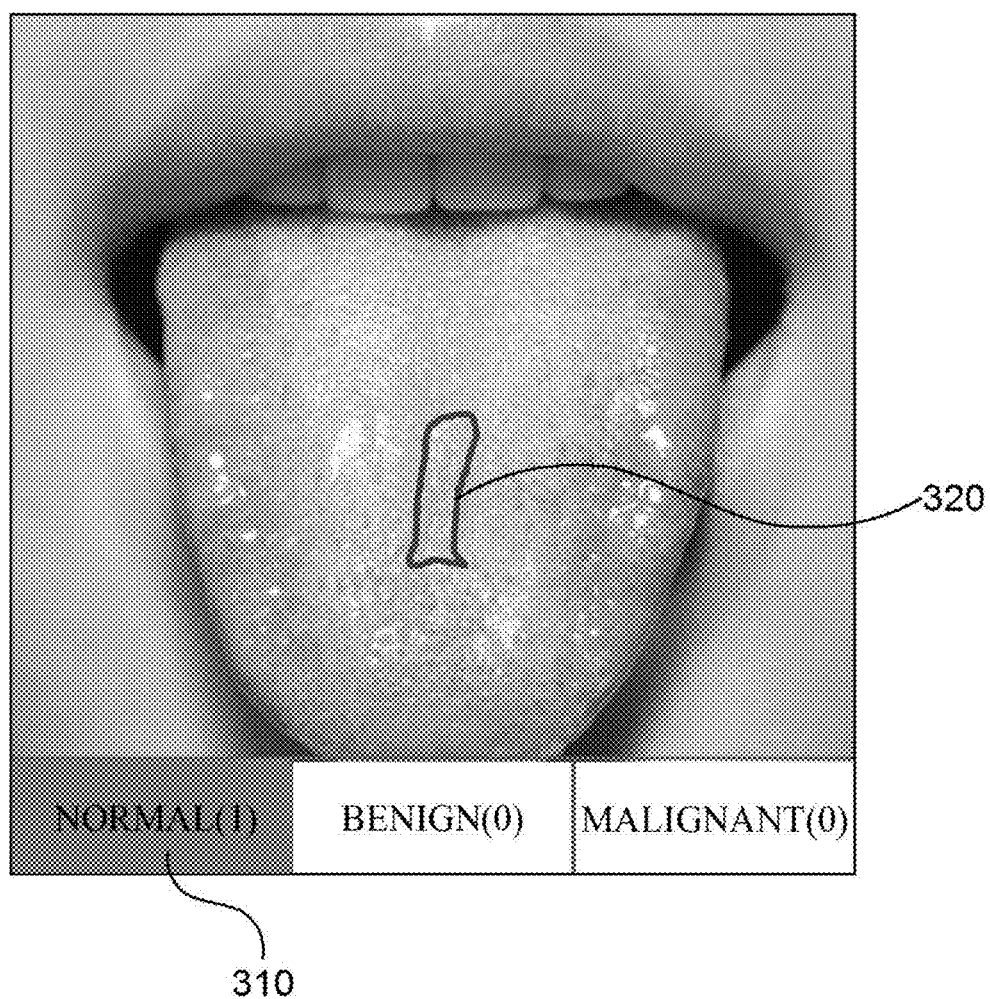
FIG. 3 is an exemplary diagram for describing a reading result according to an embodiment.

FIG. 3 is an exemplary diagram of a reading result received from a user terminal of a specific medical staff among the plurality of user terminals 300.

Referring to FIG. 3, the reading result includes the classification result of the lesion and the boundary of the lesion for the oral endoscopic image. Specifically, the lesion classification result for the oral endoscopic image corresponds to normal 310. In addition, the boundary of the lesion for the oral endoscopic image is displayed by a closed curve 320 on the oral endoscopic image.

That is, the reading result acquirer 210 can acquire the reading result including the contents is obtained by diagnosing a lesion in the corresponding oral endoscopic image as normal 310 and diagnosing an area that may be suspected of being the lesion as the closed curve 320 displayed on the oral endoscopic image by a specific medical staff.

Figure 4:
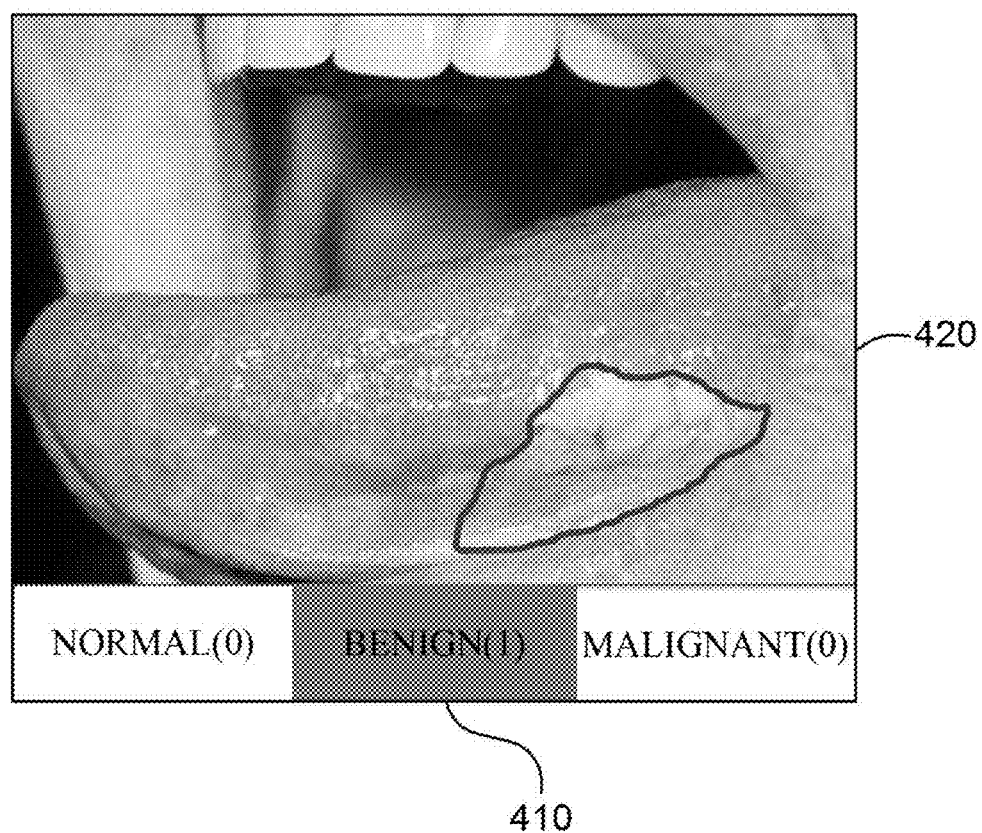
FIG. 4 is an exemplary diagram for describing another reading result according to an embodiment.

FIG. 4 is an exemplary diagram of another reading result received from the user terminal of the specific medical staff among the plurality of user terminals 300.

Referring to FIG. 4, the reading result includes the classification result of the lesion and the boundary of the lesion for the oral endoscopic image. Specifically, the lesion classification result for the oral endoscopic image corresponds to benign 410. In addition, the boundary of the lesion for the oral endoscopic image is displayed by a closed curve 420 on the oral endoscopic image.

Specifically, the lesion classification result for the oral endoscopic image illustrated in FIG. 4 corresponds to benign 410. In addition, the boundary of the lesion is an area for a portion suspected of being a lesion, and is displayed by the closed curve 420 on the corresponding oral endoscopy image.

That is, the reading result acquirer 210 can acquire the reading result including the contents obtained by diagnosing a lesion in the corresponding oral endoscopic image as normal 410 and diagnosing an area that may be suspected of being the lesion with as the closed curve 420 displayed on the oral endoscopic image by a specific medical staff.

Figure 5:
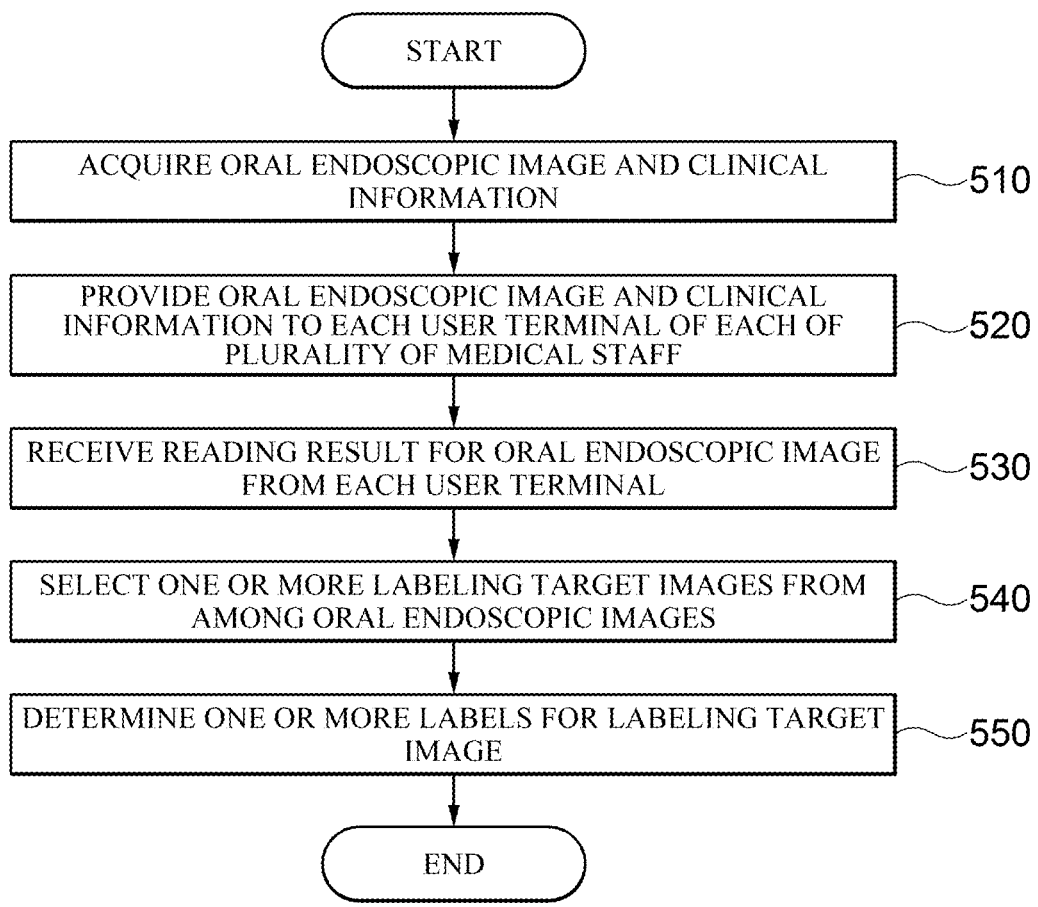
FIG. 5 is a flowchart for describing a method for generating training data according to an embodiment.

FIG. 5 is a flowchart for describing a method for generating training data according to an embodiment.

The method illustrated in FIG. 5 can be performed, for example, by the apparatus 200 for generating training data illustrated in FIG. 2.

Referring to FIG. 5, first, the apparatus 200 for generating training data acquires one or more oral endoscopic images and clinical information related to each of the one or more oral endoscopic images (510).

Thereafter, the apparatus 200 for generating training data provides the one or more oral endoscopic images and clinical information to the user terminal of each of a plurality of preset medical staffs (520).

Thereafter, the apparatus 200 for generating training data receives a reading result for each of the one or more oral endoscopic images from a user terminal of each of the plurality of medical staffs (530).

Thereafter, the apparatus 200 for generating training data selects one or more labeling target images from among one or more oral endoscopic images based on the reading result received from the user terminal of each of the plurality of medical staffs (540).

Thereafter the apparatus 200 for generating training data determines one or more labels for each of the one or more labeling target images based on the reading result (550).

Figure 6:
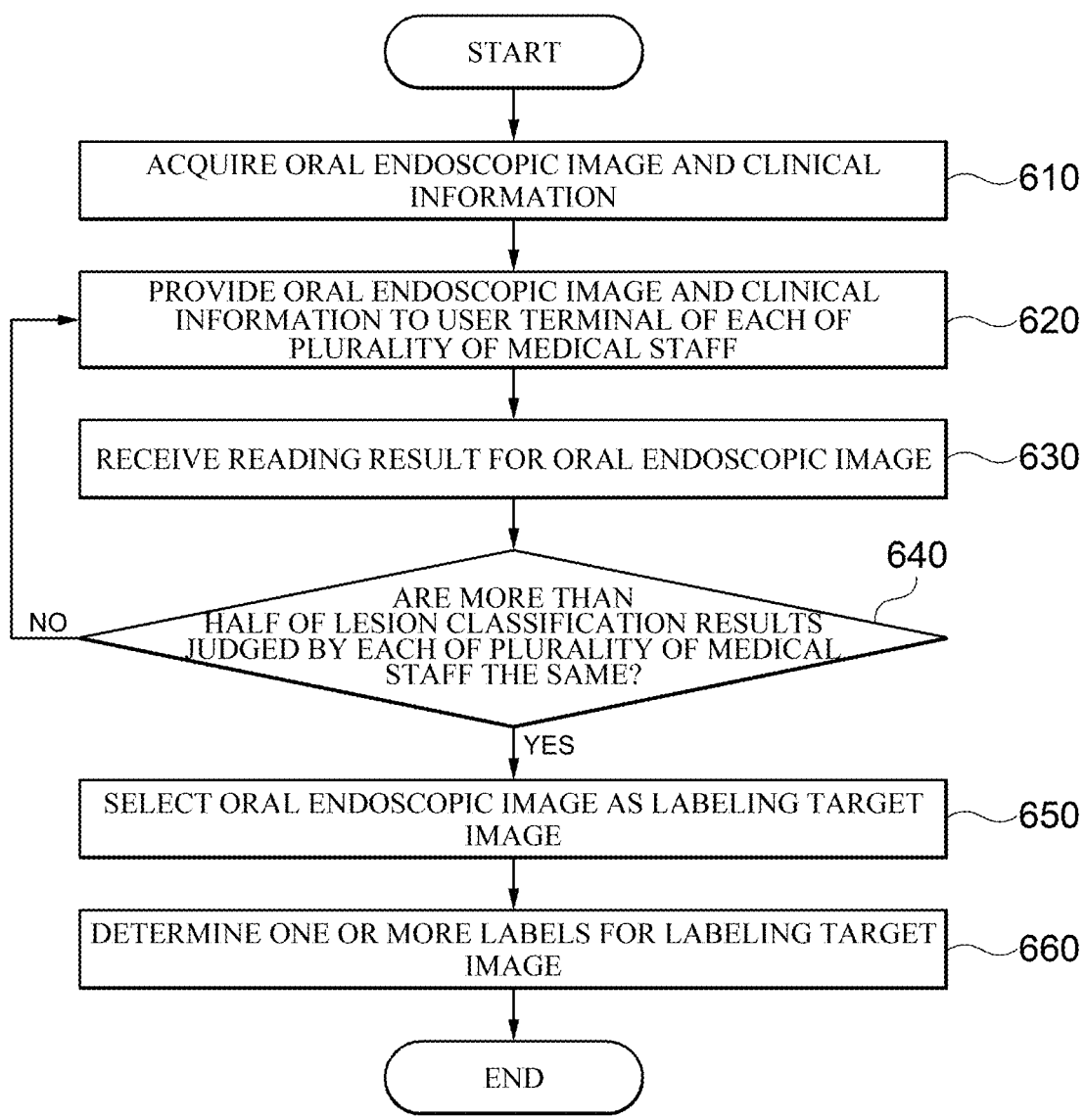
FIG. 6 is a flowchart for describing in more detail the method for generating training data according to an embodiment.

FIG. 6 is a flowchart for describing in more detail the method for generating training data according to the embodiment.

The method illustrated in FIG. 6 can be performed, for example, by the apparatus 200 for generating training data illustrated in FIG. 2.

First, the apparatus 200 for generating training data acquires the oral endoscopic image and clinical information related to each of the oral endoscopic image (610).

Thereafter, the apparatus 200 for generating training data provides the oral endoscopic image and clinical information to the user terminal of each of a plurality of preset medical staffs (620).

Thereafter, the apparatus 200 for generating training data receives a reading result for each oral endoscope image from the user terminal of each of the plurality of medical staffs (630).

Thereafter, the apparatus 200 for generating training data judges whether or not more than half of the lesion classification results judged by each of the plurality of medical staffs for the oral endoscopic image are the same based on the reading result (640).

In this case, when more than half of the lesion classification results judged by each of the plurality of medical staffs for the oral endoscope image are the same, the apparatus 200 for generating training data selects the corresponding oral endoscope image as a labeling target image (650).

Thereafter, the apparatus 200 for generating training data determines one or more labels for the labeling target image based on the reading result (660).

Meanwhile, when more than half of the lesion classification results judged by each of the plurality of medical staffs for the oral endoscopic image are not the same, the apparatus 200 for generating training data can repeatedly perform steps 620 and 630 until more than half of the lesion classification results for the oral endoscopic image are the same.

Figure 7:
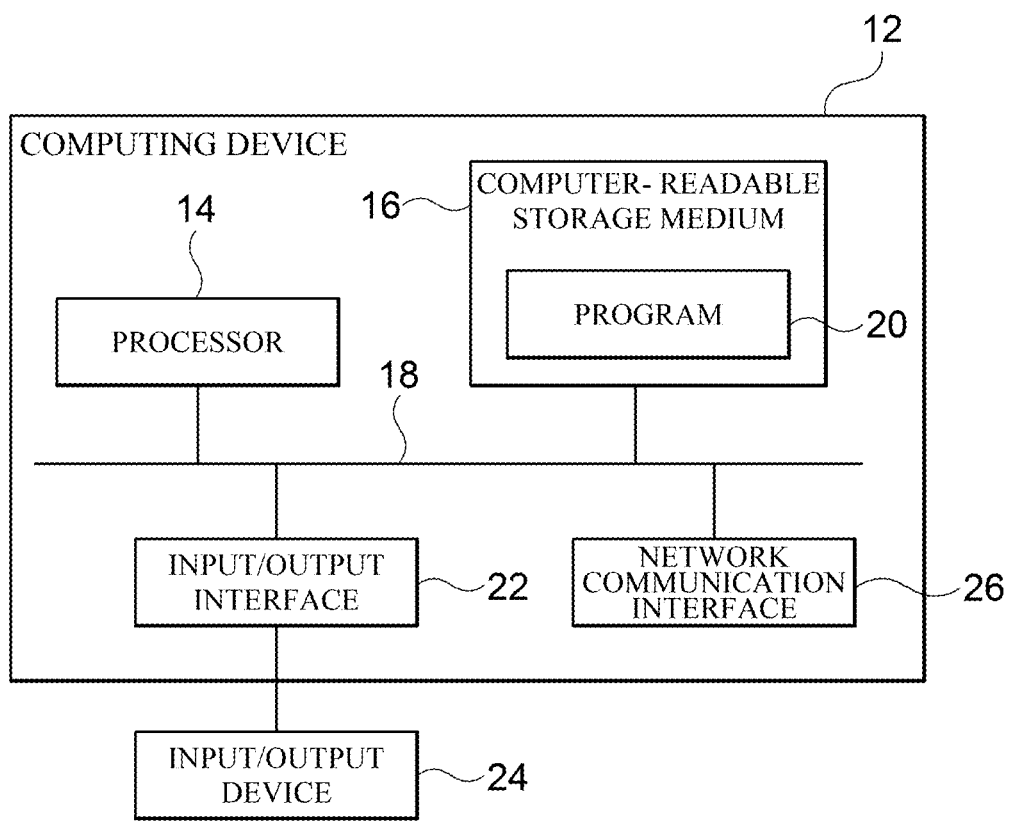
FIG. 7 is a block diagram for describing a computing device according to an embodiment.

FIG. 7 is a block diagram illustrating a computing device 12 according to an embodiment. In the illustrated embodiment, respective components may have different functions and capabilities other than those described below, and may include additional components in addition to those described below.

The illustrated computing environment 10 includes a computing device 12. In an embodiment, the computing device 12 may be one or more components included in the apparatus 200 for generating training data.

The computing device 12 includes at least one processor 14, a computer-readable storage medium 16, and a communication bus 18. The processor 14 may cause the computing device 12 to operate according to the exemplary embodiment described above. For example, the processor 14 may execute one or more programs stored on the computer-readable storage medium 16. The one or more programs may include one or more computer-executable instructions, which, when executed by the processor 14, may be configured such that the computing device 12 performs operations according to the exemplary embodiment.

The computer-readable storage medium 16 is configured such that the computer-executable instruction or program code, program data, and/or other suitable forms of information are stored. A program 20 stored in the computer-readable storage medium 16 includes a set of instructions executable by the processor 14. In one embodiment, the computer-readable storage medium 16 may be a memory (volatile memory such as a random access memory, non-volatile memory, or any suitable combination thereof), one or more magnetic disk storage devices, optical disk storage devices, flash memory devices, other types of storage media that are accessible by the computing device 12 and capable of storing desired information, or any suitable combination thereof.

The communication bus 18 interconnects various other components of the computing device 12, including the processor 14 and the computer-readable storage medium 16.

The computing device 12 may also include one or more input/output interfaces 22 that provide an interface for one or more input/output devices 24, and one or more network communication interfaces 26. The input/output interface 22 and the network communication interface 26 are connected to the communication bus 18. The input/output device 24 may be connected to other components of the computing device 12 through the input/output interface 22. The exemplary input/output device 24 may include a pointing device (such as a mouse or trackpad), a keyboard, a touch input device (such as a touch pad or touch screen), a voice or sound input device, input devices such as various types of sensor devices and/or photographing devices, and/or output devices such as a display device, a printer, a speaker, and/or a network card. The exemplary input/output device 24 may be included inside the computing device 12 as a component constituting the computing device 12, or may be connected to the computing device 12 as a separate device distinct from the computing device 12.

Although the present disclosure has been described in detail through representative examples above, those skilled in the art to which the present disclosure pertains will understand that various modifications may be made thereto within the limits that do not depart from the scope of the present disclosure. Therefore, the scope of rights of the present disclosure should not be limited to the described embodiments, but should be defined not only by claims set forth below but also by equivalents of the claims.

What is claimed is:

1. A method for generating training data, the method comprising: acquiring one or more oral endoscopic images and clinical information related to each of the one or more oral endoscopic images; providing the one or more oral endoscopic images and the clinical information to a user terminal of each of a plurality of medical staffs; receiving a reading result for each of the one or more oral endoscopic images from the user terminal of each of the plurality of medical staffs; selecting one or more labeling target images from among the one or more oral endoscopic images based on the reading result received from the user terminal of each of the plurality of medical staffs; and determining one or more labels for each of the one or more labeling target images based on the reading result, wherein the reading result includes a classification result, a boundary, and a position of a lesion included in each of the one or more oral endoscopic images, the classification result of the lesion is one of malignant, benign, or normal, the boundary of the lesion is a closed curve in the provided oral endoscopic image marked by each of the plurality of medical staffs to specify the position of the lesion, and the position of the lesion is a central position of an area surrounded by a closed curve calculated by displaying the displayed closed curve on a coordinate plane, wherein, in the determining of the one or more labels, a classification result for which more than half of the classification results of lesions judged by each of the plurality of medical staffs match is determined as a label for the labeling target image, an average position of positions of the lesions judged by each of the plurality of medical staffs is determined as a label, and an average boundary of boundaries of the lesions judged by each of the plurality of medical staffs is determined as a label.

2. The method of claim 1, wherein
in the acquiring, a malignant, an oral endoscopy image corresponding to malignant, benign, or normal is acquired based on clinical findings of a specialist on the one or more oral endoscopic images included in the clinical information.

3. The method of claim 1, wherein
the reading result includes at least one of a classification result, a position, and a boundary of a lesion included in each of the one or more oral endoscopic images.

4. An apparatus for generating training data, the apparatus comprising: a reading result acquirer that acquires one or more oral endoscopic images and clinical information related to each of the one or more oral endoscopic images, provides the one or more oral endoscopic images and the clinical information to a user terminal of each of a plurality of medical staffs, and receives a reading result for each of the one or more oral endoscopic images from the user terminal of each of the plurality of medical staffs; and a labeling unit that selects one or more labeling target images from among the one or more oral endoscopic images based on the reading result received from the user terminal of each of the plurality of medical staffs and determines one or more labels for each of the one or more labeling target images based on the reading result, wherein the reading result includes a classification result, a boundary, and a position of a lesion included in each of the one or more oral endoscopic images, the classification result of the lesion is one of malignant, benign, or normal, the boundary of the lesion is a closed curve in the provided oral endoscopic image marked by each of the plurality of medical staffs to specify the position of the lesion, and the position of the lesion is a central position of an area surrounded by a closed curve calculated by displaying the displayed closed curve on a coordinate plane, wherein the labeling unit determines a classification result for which more than half of the classification results of lesions judged by each of the plurality of medical staffs match as a label, the labeling unit determines an average position of positions of the lesions judged by each of the plurality of medical staffs as a label, and the labeling unit determines an average boundary of boundaries of the lesions judged by each of the plurality of medical staffs as a label.

5. The apparatus of claim 4, wherein
the reading result acquirer acquires an oral endoscopy image corresponding to malignant, benign, or normal based on clinical findings of a specialist on the one or more oral endoscopic images included in the clinical information.

6. The apparatus of claim 4, wherein
the reading result includes at least one of a classification result, a position, and a boundary of a lesion included in each of the one or more oral endoscopic images.

* * * * *